United States Patent [19]

Sunkel Letelier et al.

[11] 4,028,369
[45] June 7, 1977

[54] PREPARATION OF GLYCOL (2-(P-CHLOROPHENOXY)-2-METHYLPROPIONATE)-2-NICOTINATE

[75] Inventors: Carlos Sunkel Letelier, Olvega; Fernando Cillero Grafulla, Ferraz, both of Spain

[73] Assignee: Alter S.A., Madrid, Spain

[22] Filed: Aug. 4, 1975

[21] Appl. No.: 601,865

[30] Foreign Application Priority Data

June 4, 1975 Spain .................................. 438245

[52] U.S. Cl. ........................ 260/295.5 R; 424/266
[51] Int. Cl.² ........................................ C07D 213/55
[58] Field of Search ........................ 260/295.5 R

[56] References Cited

UNITED STATES PATENTS 3,622,587   11/1971   Carlson et al. ............ 260/295.5 R

OTHER PUBLICATIONS

Raphael et al., Advances in Organic Chemistry, Methods and Results, vol. 5, pp. 6 and 39, Interscience Pub. (1965).
Scherm et al., Chem. Abstracts, vol. 74, 125,446-j (1971).
Chem. Abstracts, vol. 78, 159,451-e (1973).
Chem. Abstracts, vol. 80, 3395-v, Jan. 1974.

*Primary Examiner*—Alan L. Rotman
*Attorney, Agent, or Firm*—Ladas, Parry, Von Gehr, Goldsmith & Deschamps

[57] ABSTRACT

This invention provides a process for the preparation of glycol 2-(p-chlorophenoxy)-2-methylpropionate nicotinate, of formula (I):

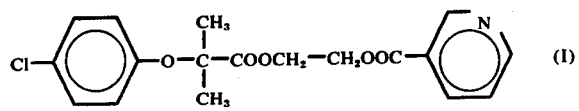

which process is characterized in that 2-(p-chlorophenoxy)-2-methylpropionic acid, of formula (II):

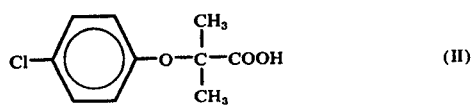

is reacted with ethylene oxide in an inert solvent in the presence of a catalyst, to prepare the monoglycol ester of the acid (II), of formula (III):

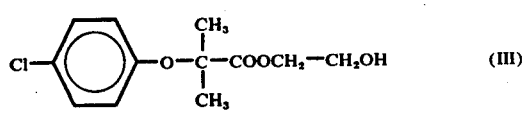

which is in turn reacted with nicotinic acid chloride in an inert solvent and in the presence of a base, to prepare the final product, of formula (I).

5 Claims, No Drawings

PREPARATION OF GLYCOL (2-(P-CHLOROPHENOXY)-2-METHYLPROPIONATE)-2-NICOTINATE

The present invention relates to a process for preparing the glycol 2-(p-chlorophenoxy)-2-methylpropionate nicotinate of formula (I), which will be called by its generic name, Ethofibrate.

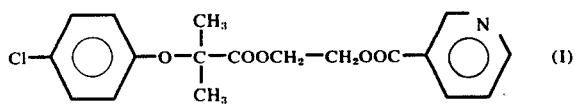

This substance is an active agent for treating arteriosclerosis and is pharmacologically more active and better tolerated than other derivatives known up to now. The process which will now be described enables Ethofibrate to be prepared, giving a high yield.

Ethofibrate can be prepared with a high degree of purity when: 2-(p-chlorophenoxy)-2-methylpropionic acid of formula (II)

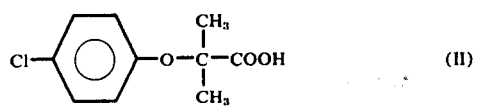

is reacted with ethylene oxide in an inert solvent such as toluene and in the presence of a Lewis acid such as zinc chloride, which serves as a catalyst. In the absence of catalyst, the yield of the reaction, in the conditions described, is considerably lower.

The product of this first reaction is the monoglycol ester of the acid (II) of formula (III):

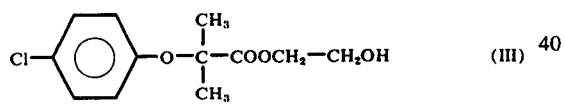

The ester (III) is reacted with nicotinic acid chloride in an inert solvent such as benzene in the presence of a base such as trimethylamine, giving the final compound (I). This compound, after being washed successively with water, dilute hydrochloric acid, ammonia and water, turns out to be an oily substance.

It should be clearly understood that neither the solvent nor the catalyst given as employed are meant to limit the invention in any way and are merely illustrative.

EXAMPLE

Preparation of glycol 2-(p-chlorophenoxy)-2-methylpropionate nicotinate

A stream of ethylene oxide is passed through a solution of 107 g of 2-(p-chlorophenoxy)-2-methylpropionic acid and 2 g of zinc chloride in 200 ml of toluene, previously heated to between 55° and 60° C., until 24 g of the gas have been dissolved. The reaction is allowed to continue for five hours, with gentle stirring. After this time has elapsed, the solution is cooled and washed successively with water, dilute ammonia and water until its pH becomes neutral. It is dried over anhydrous sodium sulfate, the solvent is separated off under vacuum, and the resulting liquid is the monoglycol ester of 2-(p-chlorophenoxy)-2-methylpropionic acid.

The product thus prepared is sufficiently pure to be used in the subsequent reaction. In this way, 107 grams of the ester are prepared, which represents a yield of 83%.

To a solution of 93.8 g of the monoglycol ester in 500 ml of benzene, there are added 55 g of nicotinic acid chloride and 25 g of trimethylamine dissolved in 200 ml of benzene. The solution is stirred gently at a temperature of 60° C. for two hours. After this time, the solution is cooled and washed successively with water, dilute hydrochloric acid, dilute ammonia and water until neutrality, it is dried over anhydrous sodium sulfate, and the solvent is evaporated under vacuum: in this way 110 g of glycol 2-(p-chlorophenoxy)-2-methylpropionate nicotinate is prepared, which represents a yield of 84%. The product is a slightly yellow oil having a refraction index of $n_D^{20} = 1.5422$ and which is distilled with decomposition at 214° C. at a pressure of 0.3 mm.

Analysis calculated for $C_{18}H_{18}ClNO_5$: C: 59.43%; H: 4.99%; Cl: 9.75%; N: 3.85% Found: C: 59.34%; H: 4.77%; Cl: 10.03%; N: 3.68%

We claim:

1. A process for the preparation of glycol 2-(p-chlorophenoxy)-2-methylpropionate nicotinate, of formula (I):

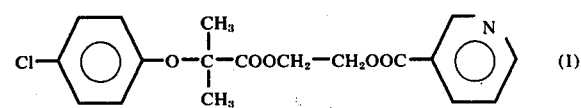

which process is characterized in that 2-(p-chlorophenoxy)-2-methylpropionic acid, of formula (II):

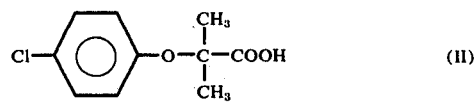

is reacted with ethylene oxide at a temperature of up to about 60° C in an inert solvent in the presence of a zinc chloride as a catalyst, to prepare the monoglycol ester of the acid (II), of formula (III):

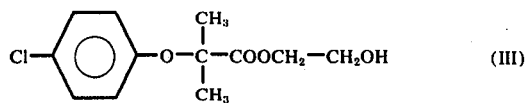

which is in turn reacted with nicotinic acid chloride in an inert solvent and in the presence of a base at a temperature of up to about 60° C, to prepare the final product, of formula (I).

2. A process for the preparation of glycol 2-(p-chlorophenoxy)-2-methylpropionate nicotinate, as claimed in claim 1, characterized in that the solvent employed in the reaction of the ester (III) with nicotinic acid chloride is benzene.

3. A process for the preparation of glycol 2-(p-chlorophenoxy)-2-methylpropionate nicotinate, as claimed in claim 1, characterized in that for the reaction of the ester (III) with nicotinic acid chloride the base employed is trimethylamine.

4. A process for the preparation of glycol 2-(p-chlorophenoxy)-2-methylpropionate nicotinate, as claimed in claim 1, characterized in that the solvent employed in the reaction of the ester (III) with nicotinic acid chloride is benzene.

5. A process for the preparation of glycol 2-(p-chlorophenoxy)-2-methylpropionate nicotinate, as claimed in claim 1, characterized in that the solvent employed in the reaction of the acid (II) with ethylene oxide is toluene.

* * * * *